United States Patent
Oguchi et al.

(10) Patent No.: US 9,040,743 B2
(45) Date of Patent: May 26, 2015

(54) METHOD FOR PRODUCING N-PROPYL ACETATE AND METHOD FOR PRODUCING ALLYL ACETATE

(75) Inventors: Wataru Oguchi, Kawasaki (JP); Hiroshi Maruta, Oita (JP)

(73) Assignee: SHOWA DENKO K.K., Tokyo (JP)

( * ) Notice: Subject to any disclaimer, the term of this patent is extended or adjusted under 35 U.S.C. 154(b) by 204 days.

(21) Appl. No.: 13/637,834

(22) PCT Filed: Mar. 14, 2011

(86) PCT No.: PCT/JP2011/056514
§ 371 (c)(1),
(2), (4) Date: Sep. 27, 2012

(87) PCT Pub. No.: WO2011/122367
PCT Pub. Date: Oct. 6, 2011

(65) Prior Publication Data
US 2013/0018203 A1    Jan. 17, 2013

(30) Foreign Application Priority Data
Mar. 31, 2010   (JP) ................................ 2010-079950

(51) Int. Cl.
*C07C 67/58* (2006.01)
*C07C 67/54* (2006.01)
*C07C 67/283* (2006.01)
*C07C 67/055* (2006.01)

(52) U.S. Cl.
CPC ............. *C07C 67/055* (2013.01); *C07C 67/283* (2013.01); *C07C 67/54* (2013.01); *C07C 67/58* (2013.01)

(58) Field of Classification Search
CPC ........ C07C 67/58; C07C 67/54; C07C 67/283
USPC ....................................... 560/248
See application file for complete search history.

(56) References Cited

U.S. PATENT DOCUMENTS

2011/0065951 A1    3/2011   Hatanaka et al.

FOREIGN PATENT DOCUMENTS

| CN | 1733685 A | 2/2006 |
|---|---|---|
| CN | 101389584 A | 3/2009 |
| JP | 61-238759 A | 10/1986 |
| JP | 62-149637 A | 7/1987 |
| JP | 3-109358 A | 5/1991 |
| JP | 7-206724 A | 8/1995 |
| JP | 9-194427 A | 7/1997 |
| JP | 2009-120526 A | 6/2009 |
| TW | 201008908 A1 | 3/2010 |
| WO | 00/64852 A1 | 2/2000 |
| WO | 2009/064012 A1 | 5/2009 |
| WO | 2009/142245 A1 | 11/2009 |
| WO | WO 2009142245 A1 * | 11/2009 |

OTHER PUBLICATIONS

Office Action for corresponding Taiwanese Application 100109891 Dated Apr. 23, 2013.
Japanese Office Action for corresponding Application No. 2010-079950, mail date Mar. 11, 2014, 8 pages.
Chinese Office Action for corresponding Application No. 201180016439.8, issued Feb. 8, 2014, 14 pages.

* cited by examiner

*Primary Examiner* — Yong Chu
(74) *Attorney, Agent, or Firm* — Sughrue Mion, PLLC

(57) ABSTRACT

Provided is a method for producing n-propyl acetate, which is capable of obtaining high-purity allyl acetate with a low amount of coexisting water and is capable of producing n-propyl acetate with a high yield. The method includes an extraction process of subjecting a raw material liquid containing allyl acetate and water to an extraction operation using water as an extraction solvent and separating the extract into an oily phase and an aqueous phase, a distillation process of distilling the oily phase to obtain a distillate containing allyl acetate as a main component, and a hydrogenation process of subjecting the distillate to a hydrogenation reaction.

9 Claims, 2 Drawing Sheets

METHOD FOR PRODUCING N-PROPYL ACETATE AND METHOD FOR PRODUCING ALLYL ACETATE

CROSS REFERENCE TO RELATED APPLICATIONS

This application is a National Stage of International Application No. PCT/JP2011/056514 filed Mar. 14, 2011, claiming priority based on Japanese Patent Application No. 2010079950 filed Mar. 31, 2010, the contents of which are incorporated herein by reference in their entirety.

TECHNICAL FIELD

The present invention relates to a method for producing n-propyl acetate and a method for producing allyl acetate.

BACKGROUND ART

Conventionally, saturated carboxylic acid esters, such as ethyl acetate, n-propyl acetate, isobutyl acetate and n-butyl acetate, have been widely used as a solvent or a reaction solvent, and they are industrially important compounds.

These saturated carboxylic acid esters may be produced by a hydrogenation reaction of unsaturated carboxylic acid esters of corresponding chemical structures.

As the method for producing unsaturated carboxylic acid esters, there are several methods.

Specific examples thereof include a production method of an esterification reaction of unsaturated alcohol and carboxylic acid, and a production method of an oxidative carboxylation reaction using a carboxylic acid, oxygen and an olefin compound.

For example, the method for producing allyl acetate generally includes a method for producing allyl acetate by the esterification reaction of allyl alcohol and acetic acid or by the oxidative carboxylation reaction of propylene, acetic acid and oxygen.

In such an esterification reaction or oxidative carboxylation reaction, allyl acetate and water are simultaneously produced. For this reason, allyl acetate obtained by such a reaction generally contains water as a by-product and unreacted acetic acid as impurities. That is, industrially available allyl acetate is any of allyl acetate containing water, or allyl acetate from which water has been removed by a certain method.

For example, in the oxidative carboxylation reaction of propylene, acetic acid and oxygen, allyl acetate and water are produced, as shown in the Reaction Scheme below.

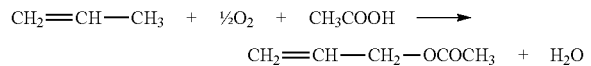

When unsaturated carboxylic acid esters are produced by the esterification reaction of unsaturated alcohol and carboxylic acid, generally, since there is a reaction equilibrium in the esterification reaction of unsaturated alcohol and carboxylic acid, unsaturated alcohol and carboxylic acid raw materials, in addition to the products of unsaturated carboxylic acid ester and water, also remain in the reaction mixture after reaching a steady-state. Therefore, when unsaturated carboxylic acid esters are subjected to a hydrogenation reaction, it is necessary to separate high-purity unsaturated carboxylic acid esters from the reaction mixture, after the esterification reaction of unsaturated alcohol and carboxylic acid.

On the other hand, as the method for producing unsaturated carboxylic acid esters by the oxidative carboxylation reaction using a carboxylic acid, oxygen and an olefin compound, Patent Citation 1 discloses a method for producing allyl acetate by the gas-phase reaction of propylene, oxygen and acetic acid in the presence of a palladium catalyst. According to this production method, it is stated that allyl acetate can be industrially produced advantageously.

However, unreacted carboxylic acid which is a raw material, in addition to unsaturated carboxylic acid ester which is the product of an oxidative carboxylation reaction and water, is frequently included in the mixture obtained from the reactor outlet. Therefore, when unsaturated carboxylic acid esters are subjected to a hydrogenation reaction, it is necessary to separate high-purity unsaturated carboxylic acid esters from the mixture obtained after the oxidative carboxylation reaction.

Further, when unsaturated carboxylic acid esters are subjected to a hydrogenation reaction, an isomerization reaction or hydrogenation decomposition reaction which is a minor reaction may be accompanied, in conjunction with a hydrogenation reaction which is a major reaction. For this reason, the hydrogenation reaction of unsaturated carboxylic acid esters is required to exhibit suppression of a minor reaction as much as possible.

Patent Citation 2 discloses a production method including subjecting unsaturated carboxylic acid ester to a hydrogenation reaction in the presence of a nickel-based hydrogenation catalyst, as the method for producing saturated carboxylic acid esters. According to this production method, it is believed that saturated carboxylic acid ester can be produced with a high yield by suppressing a hydrogenation decomposition reaction.

PATENT CITATION 1

JP-A-61-238759
JP-A-9-194427

DISCLOSURE OF INVENTION

Technical Problem

In the invention disclosed in Patent Citation 2, regarding selectivity and yield when producing saturated carboxylic acid ester, for example, a conversion rate of allyl acetate in the hydrogenation reaction of allyl acetate is 96.5%, a selectivity of n-propyl acetate is 96.2%, and a yield of n-propyl acetate is 92.8%, which are not industrially sufficient.

As a result of investigation, the inventors of the present invention found that, for example, when n-propyl acetate is produced, the hydrogenation reaction of allyl acetate is readily susceptible to the occurrence of a minor reaction due to the effects of water produced concurrently with allyl acetate through an oxidative carboxylation reaction, and production of n-propyl acetate with a high yield becomes difficult.

Since allyl acetate and at least an equimolar amount of water are simultaneously produced in the oxidative carboxylation reaction, the concentration of water in the mixture of allyl acetate and water obtained after this reaction is about 15% by mass from the relationship of molecular weight. On the other hand, allyl acetate and water have an azeotropic composition, and water in the azeotropic composition accounts for a molar fraction of 53 mol % and a weight portion of 16.7% by mass.

Therefore, when the mixture of allyl acetate and water obtained by the oxidative carboxylation reaction is simply distilled, the composition of the distillate is virtually the same as that of the mixture obtained by the oxidative carboxylation reaction, and it is difficult to lower the concentration of water in the distillate containing allyl acetate by a simple distillation operation.

As the method of lowering the concentration of water other than the simple distillation operation, a combination of a distillation operation with another separation operation can be contemplated.

For example, when raw material liquid (crude allyl acetate) containing allyl acetate and water forms two phases of an oily phase and an aqueous phase, a method can be contemplated including separating the raw material liquid into an oily phase containing allyl acetate as a main component and an aqueous phase using an oil-water separation unit (for example, decanter) and then subjecting the oily phase to distillation.

However, since the water concentration in the oily phase containing allyl acetate as a main component, after the oil-water separation, is at least about 2% by mass, even by a combination of this oil-water separation operation and a distillation operation, there is a limit associated with lowering of the water concentration in the distillate obtained by a subsequent distillation operation.

Further, as described above, when unsaturated carboxylic acid esters are produced by the esterification reaction of unsaturated alcohol and carboxylic acid or by the oxidative carboxylation reaction using carboxylic acid, oxygen and olefin compound, unreacted raw materials, in addition to unsaturated carboxylic acid esters and water, generally remain in the reaction mixture.

Specifically, due to the reaction equilibrium of esterification, acetic acid and allyl alcohol, in addition to allyl acetate and water, remain in the reaction mixture for the esterification reaction of allyl alcohol and acetic acid, so that the reaction mixture becomes a 4-component mixture.

On the other hand, when allyl acetate is produced by the oxidative carboxylation reaction of propylene, acetic acid and oxygen, the reaction mixture is obtained by condensing the gases from the reactor outlet, as described in Patent Citation 1, and the reaction mixture is a 3-component mixture of allyl acetate, acetic acid and water.

It is more difficult to obtain high-purity allyl acetate from such a 3-component or 4-component mixture, as compared to obtaining of allyl acetate from the 2-component mixture of allyl acetate and water.

As discussed above, according to a general method for producing allyl acetate, the obtained reaction mixture becomes a multi-component system, and it is difficult to separate allyl acetate with high purity from the reaction mixture.

The present invention has been made in view of the above situation, and it is an object of the present invention to provide a method which is capable of obtaining high-purity allyl acetate with a lower amount of coexisting water and is capable of producing n-propyl acetate with a high yield.

Technical Solution

As a result of intensive investigation to accomplish the object, the inventors of the present invention found that allyl acetate with a reduced amount of coexisting water is obtained by carrying out an extraction operation using water as an extraction solvent in combination with a distillation operation. The present invention has been completed based on these findings.

That is, the present invention relates to the following [1] to [10].

[1] A method for producing n-propyl acetate, including an extraction process of subjecting a raw material liquid containing allyl acetate and water to an extraction operation using water as an extraction solvent and separating the extract into an oily phase and an aqueous phase, a distillation process of distilling the oily phase to obtain a distillate containing allyl acetate as a main component, and a hydrogenation process of subjecting the distillate to a hydrogenation reaction.

[2] The method for producing n-propyl acetate according to [1], including
an extraction process of subjecting a raw material liquid containing allyl acetate and water to an extraction operation using water as an extraction solvent and separating the extract into an oily phase (B) containing allyl acetate as a main component and an aqueous phase (B) containing water as a main component, a first distillation process of distilling the oily phase (B) to obtain distillate (X) containing allyl acetate as a main component, an oil-water separation process of separating the distillate (X) into an oily phase (C) and an aqueous phase (C), a second distillation process of distilling the oily phase (C) to obtain a distillate (Y) containing allyl acetate as a main component, and a hydrogenation process of subjecting the distillate (Y) to a hydrogenation reaction.

[3] The method for producing n-propyl acetate according to [2], wherein the aqueous phase (C) is returned to the first distillation process.

[4] The method for producing n-propyl acetate according to [2] or [3], including a third distillation process of further distilling the distillate (Y) between the second distillation process and the hydrogenation process.

[5] The method for producing n-propyl acetate according to any one of [1] to [4], including a process for preparing a raw material liquid, for preparing the raw material liquid by an oxidative carboxylation reaction using propylene, acetic acid and oxygen gas as raw materials, before the extraction process.

[6] The method for producing n-propyl acetate according to any one of [1] to [5], wherein the concentration of water (by mass) in the distillate for use in the hydrogenation reaction is 1000 ppm or less.

[7] The method for producing n-propyl acetate according to [6], wherein the concentration of water (by mass) in the distillate for use in the hydrogenation reaction is 100 ppm or less.

[8] The method for producing n-propyl acetate according to any one of [1] to [7], wherein a catalyst including at least one selected from platinum, palladium, rhodium, ruthenium and nickel is used in the hydrogenation reaction.

[9] A method for producing n-propyl acetate, including subjecting a raw material containing allyl acetate and water at a concentration (by mass) of 100 ppm or less to a hydrogenation reaction.

[10] A method for producing allyl acetate, including a reaction process of carrying out an oxidative carboxylation reaction using propylene, acetic acid and oxygen gas as raw materials, an extraction process of subjecting the reaction mixture obtained in the reaction process to an extraction operation using water as an extraction solvent and separating the extract into an oily phase and an aqueous phase, and a distillation process of distilling the oily phase.

The term "main component" in the present invention refers to a component whose content in an oily phase, aqueous phase or distillate accounts for 50% by mass or more.

Advantageous Effects

The method for producing n-propyl acetate in accordance with the present invention enables the production of n-propyl acetate with a high yield.

Further, the method for producing allyl acetate in accordance with the present invention is capable of obtaining high-purity allyl acetate with a low amount of coexisting water.

EXPLANATION OF REFERENCE

Figure 1:
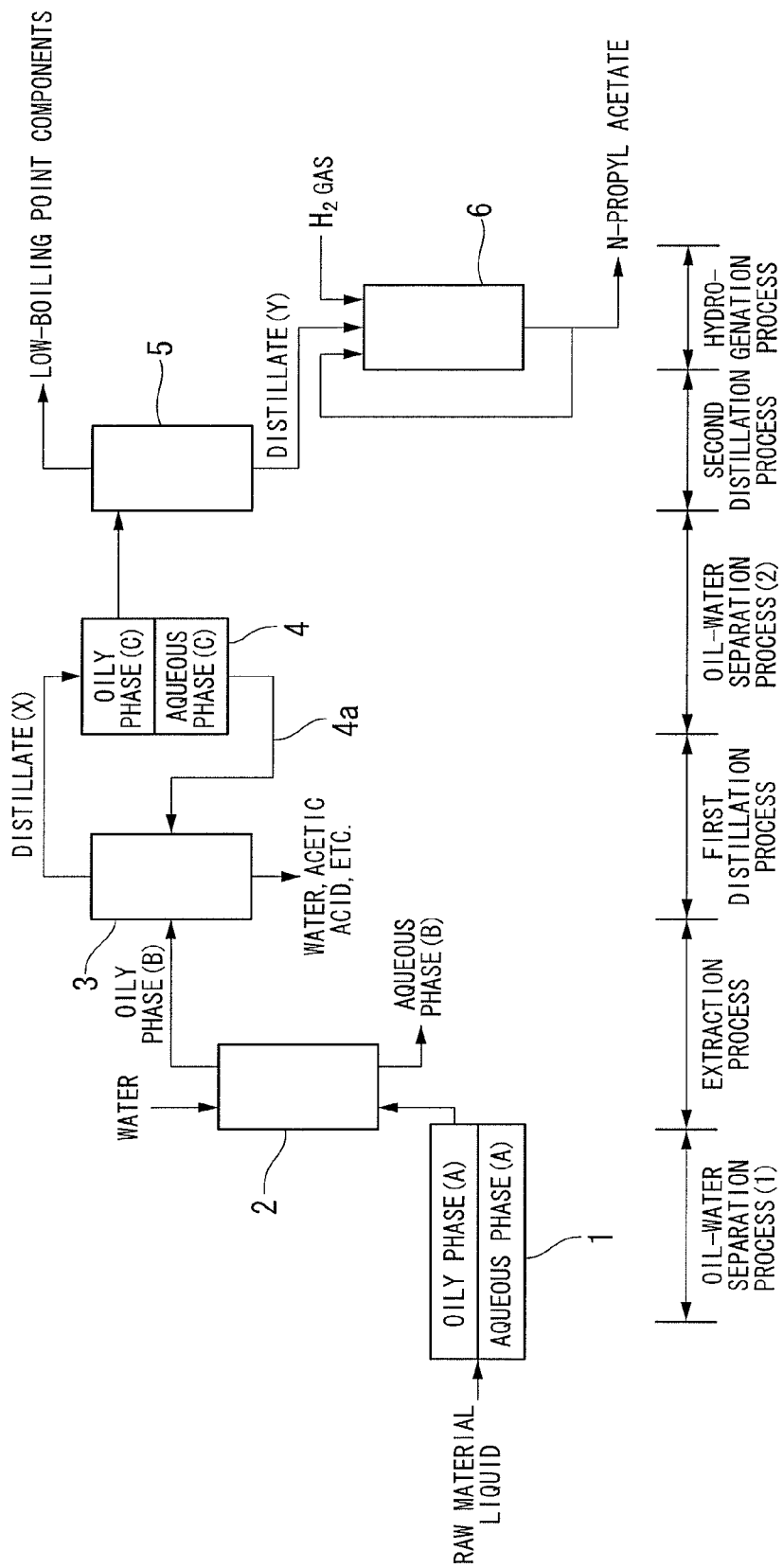
FIG. 1 is a schematic flow chart illustrating one exemplary embodiment of a method for producing n-propyl acetate in accordance with the present invention.

1: oil-water separation unit
2: extraction column
3: first distillation column
4: oil-water separation unit
5: second distillation column
6: hydrogenation reactor
7: reactor
8: gas-liquid separator

BEST MODE FOR CARRYING OUT THE INVENTION

<Method for Producing n-propyl Acetate (1)>

The method for producing n-propyl acetate (1), which is the first embodiment of the present invention, includes an extraction process of subjecting a raw material liquid containing allyl acetate and water to an extraction operation using water as an extraction solvent and separating the extract into an oily phase and an aqueous phase, a distillation process of distilling the oily phase to obtain a distillate containing allyl acetate as a main component, and a hydrogenation process of subjecting the distillate to a hydrogenation reaction.

FIG. 1 is a schematic flow chart illustrating one exemplary embodiment of a method for producing n-propyl acetate in accordance with the present invention.

The present exemplary embodiment includes an extraction process, a distillation process and a hydrogenation process, wherein the distillation process includes a first distillation process and a second distillation process. Further, oil-water separation processes are included before the extraction process and between the first distillation process and the second distillation process, respectively.

According to the present exemplary embodiment, first, in the oil-water separation process (1) before the extraction process, a raw material liquid containing allyl acetate and water is separated into an oily phase (A) containing allyl acetate as a main component and an aqueous phase (A) containing water as a main component.

Then, in the extraction process, the oily phase (A) is subjected to an extraction operation using water as an extraction solvent, and the extract is separated into an oily phase (B) containing allyl acetate as a main component and an aqueous phase (B) containing water as a main component.

Next, in the first distillation process, the oily phase (B) is distilled to obtain a distillate (X) containing allyl acetate as a main component; in the oil-water separation process (2) after carrying out the first distillation process, the distillate (X) is separated into an oily phase (C) and an aqueous phase (C); and then, in the second distillation process, the oily phase (C) is distilled to obtain a distillate (Y) containing allyl acetate as a main component.

Thereafter, in the hydrogenation process, the distillate (Y) is subjected to a hydrogenation reaction to produce n-propyl acetate.

The raw material liquid containing allyl acetate and water may be prepared, for example, by a method for preparing a raw material liquid (1) through an oxidative carboxylation reaction using propylene, acetic acid and oxygen gas as raw materials, a method for preparing a raw material liquid (2) through an esterification reaction of allyl alcohol and carboxylic acid, a method for preparing a raw material liquid (3) through a reaction of propylene chloride and carboxylic acid or a salt thereof, or the like.

The content of allyl acetate in the raw material liquid is preferably 40% by mass or more, and more preferably 50 to 60% by mass. If the content of allyl acetate is less than 40% by mass, oil-water separation becomes difficult, which may result in deterioration of oil-water separation efficiency in the oil-water separation process (1) in the present exemplary embodiment.

The content of water in the raw material liquid is preferably 35% by mass or less, and more preferably 20% by mass or less. If the content of water is excessively high, at more than 35% by mass, oil-water separation becomes difficult, which may result in deterioration of oil-water separation efficiency in the oil-water separation process (1) in the present exemplary embodiment.

Further, the raw material liquid containing allyl acetate and water may contain unreacted acetic acid, if necessary, in addition to allyl acetate and water.

The present exemplary embodiment includes an oil-water separation process (1) before the extraction process.

In the oil-water separation process (1), a raw material liquid is separated into an oily phase (A) containing allyl acetate as a main component and an aqueous phase (A) containing water as a main component, using an oil-water separation unit 1.

In the method for producing n-propyl acetate in accordance with the present invention, although the oil-water separation process (1) is not essential, it is preferable that the raw material liquid be separated in advance into an oily phase (A) and an aqueous phase (A), and only the oily phase (A) with a high concentration of allyl acetate be supplied to an extraction process. Accordingly, high-purity allyl acetate with a low amount of coexisting water is easily obtained in the extraction process.

The operation of oil-water separation may be carried out by standing separation, centrifugation or the like. For example, an oil-water separation unit such as a decanter may be used for oil-water separation.

[Extraction Process]

In the extraction process in accordance with the present exemplary embodiment, the oily phase (A) obtained in the oil-water separation process (1) is subjected to an extraction operation using water as an extraction solvent, and then the extract is separated into the oily phase (B) containing allyl acetate as a main component and the aqueous phase (B) containing water as a main component.

Specifically, the oily phase (A) is supplied from the column bottom of an extraction column 2, and water as an extraction solvent is supplied from the column top of an extraction column 2, whereby the oily phase (A) is brought into contact with water in the extraction column 2. Then, the extract is separated into the oily phase (B) containing allyl acetate as a main component, and the aqueous phase (B) containing water as a main component and containing acetic acid and the like. The oily phase (B) is obtained from the column top, and the aqueous phase (B) is removed from the column bottom.

The temperature of the oily phase (A) and water supplied to the extraction column 2 is not particularly limited. The supply amount of water to the extraction column 2 is preferably in the range of 40 to 100 parts by mass based on 100 parts by mass of the oily phase (A), and more preferably 50 to 70 parts by mass. If the supply amount of water is less than the lower limit, the extraction efficiency of water and acetic acid from the oily phase (A) is deteriorated. On the other hand, if the supply amount of water is higher than the upper limit, costs are incurred for the treatment of the aqueous phase (B) (drainage treatment).

The contact time between the oily phase (A) and water is preferably 5 minutes or longer, and more preferably 15 to 30 minutes. If the contact time is the lower limit or longer, oily phase (A) and water may be favorably separated.

In the method for producing n-propyl acetate in accordance with the present invention, high-purity allyl acetate with a low amount of coexisting water is obtained by carrying out the extraction operation before the distillation process.

[Distillation Process]

In the distillation process, the oily phase obtained in the extraction process is distilled to a distillate containing allyl acetate as a main component.

The present exemplary embodiment includes a first distillation process and a second distillation process.

(First Distillation Process)

In the first distillation process, the oily phase (B) obtained in the extraction process is distilled to obtain a distillate (X) containing allyl acetate as a main component.

Specifically, the oily phase (B) is supplied to a first distillation column 3, followed by distillation. The distillate (X) containing allyl acetate as a main component is obtained from the column top of the distillation column 3 while high-boiling point components including acetic acid are removed from the column bottom.

With regard to the distillation conditions for the first distillation process, for the purpose of further reducing the amount of water coexisting with allyl acetate and obtaining allyl acetate with a high yield, the top pressure of the distillation column is preferably in the range of 0 to 200 kPaG (gauge pressure), more preferably 20 to 100 kPaG, and the bottom pressure is preferably in the range of 10 to 210 kPaG, more preferably 30 to 110 kPaG.

The top temperature of the distillation column is preferably in the range of 85 to 120° C., more preferably 95 to 105° C., and the bottom temperature is preferably in the range of 105 to 150° C., more preferably 110 to 120° C.

The reflux ratio is preferably in the range of 0.1 to 0.5, more preferably 0.1 to 0.2, and the evaporation rate is preferably 80% by mass or more, more preferably 90% by mass or more.

As used herein, the term "top pressure", the term "bottom pressure", the term "top temperature", and the term "bottom temperature" refer to gauge pressures and temperatures as measured at the top and bottom of a distillation column, respectively, wherein the top is a column top from which a distillate is discharged, and the bottom is a column bottom in which residues are collected.

The term "reflux ratio" refers to a ratio of a reflux liquid amount to a distillate amount.

The term "evaporation rate" represents a ratio (% by mass) of a distillate amount to an injected (supplied) liquid amount. A higher evaporation rate is preferable. If the evaporation rate is high, an amount of recoverable allyl acetate is increased, thus improving a product yield.

The present exemplary embodiment includes an oil-water separation process (2) after the first distillation process.

In the oil-water separation process (2), the distillate (X) obtained in the first distillation process is separated into an oily phase (C) and an aqueous phase (C), using an oil-water separation unit 4.

In the method for producing n-propyl acetate in accordance with the present invention, although the oil-water separation process (2) is not essential, it is preferable that the distillate (X) be separated into the oily phase (C) containing allyl acetate as a main component and the aqueous phase (C) containing water as a main component, and only the oily phase (C) with a high concentration of allyl acetate be supplied to a subsequent second distillation process. In this manner, in the second distillation process, the amount of water coexisting with allyl acetate can be further reduced.

The operation of oil-water separation may be carried out by standing separation, centrifugation or the like. For example, an oil-water separation unit such as a decanter may be used for oil-water separation.

Further, the present exemplary embodiment is configured such that an aqueous phase portion of an oil-water separation unit 4 and the first distillation column 3 are connected to a flow channel 4a, and the aqueous phase (C) is returned to the first distillation column 3.

As described above, returning of the aqueous phase (C) obtained in the oil-water separation process (2) to the first distillation process and re-distillation thereof are preferable since allyl acetate contained in the aqueous phase (C) can be recovered, and allyl acetate is obtained with a high yield.

Further, although not shown in the figure, an oily phase portion of the oil-water separation unit 4 may be connected with the first distillation column 3 through a flow channel, whereby the oily phase (C) obtained in the oil-water separation process (2) is partially returned to the first distillation process, followed by re-distillation. Particularly, when the composition of the distillate (X) has a relatively high water concentration as compared to the azeotropic composition of water and allyl acetate, carrying out the operation (re-distillation) may further remove water from the oily phase (C), so that the composition of the distillate (X) approximates to the azeotropic composition of water and allyl acetate.

(Second Distillation Process)

In the second distillation process, the oily phase (C) obtained in the oil-water separation process (2) is distilled to a distillate (Y) containing allyl acetate as a main component.

Specifically, the oily phase (C) obtained in the oil-water separation process (2) is supplied to a second distillation column 5, followed by distillation. The distillate (Y) containing allyl acetate as a main component is obtained from the column bottom of the distillation column while low-boiling point components having a lower boiling point than allyl acetate are removed from the column top.

With regard to the distillation conditions for the second distillation process, for the purpose of removing components having a lower boiling point than allyl acetate and obtaining allyl acetate with higher purity, the top pressure of the distillation column is preferably in the range of 50 to 200 kPaG, more preferably 100 to 200 kPaG, and the bottom pressure is preferably in the range of 60 to 210 kPaG, more preferably 110 to 180 kPaG.

The top temperature of the distillation column is preferably in the range of 100 to 135° C., more preferably 110 to 120° C., and the bottom temperature is preferably in the range of 120 to 150° C., more preferably 130 to 140° C.

The reflux ratio is preferably in the range of 8 to 12, and more preferably 10 to 12.

In the second distillation process, since the desired purified allyl acetate is withdrawn as a residue from the column bottom, the evaporation rate in the second distillation process is preferably low and the evaporation rate is preferably 12% by mass or less, more preferably 8% by mass or less.

In the present exemplary embodiment, the distillate (Y) obtained in the second distillation process is supplied to a subsequent hydrogenation process, followed by hydrogenation reaction.

According to the present exemplary embodiment, the concentration of allyl acetate in the distillate (Y) obtained in the second distillation process can be preferably set to 99.00% by mass or more, more preferably 99.50% by mass or more, and particularly preferably 99.60% by mass or more.

In this manner, high-purity allyl acetate is obtained according to the present exemplary embodiment. Further, if the concentration of allyl acetate is 99.00% by mass or more, n-propyl acetate can be produced with a high yield.

Further, according to the present exemplary embodiment, the concentration of water (by mass) in the distillate (Y) can be preferably set to 1000 ppm or less, more preferably 500 ppm or less, still more preferably 100 ppm or less, and particularly preferably 50 ppm or less.

If the concentration of water is high, when a hydrogenation reaction is carried out, the isomerization reaction of allyl acetate results in production of 1-propenyl acetate as a by-product, the hydrogenation decomposition reaction results in significant production of acetic acid and/or propane as by-products, and further, acetic acid produced as a by-product inhibits the hydrogenation reaction of allyl acetate. For these reasons, the concentration of water (by mass) is preferably set to 1000 ppm or less.

From the viewpoint of avoiding the isomerization reaction of allyl acetate, a more preferable concentration of water (by mass) is 500 ppm or less. Further, in order to avoid catalyst poisoning due to the production of acetic acid as a by-product, a particularly preferable concentration of water (by mass) is 50 ppm or less.

Further, according to the present exemplary embodiment, the concentration (by mass) of allyl acrylate in the distillate (Y) obtained in the second distillation process can be set to 3000 ppm or less, and the concentration (by mass) of acetic acid can be set to 500 ppm or less.

[Hydrogenation Process]

In the hydrogenation process of the present exemplary embodiment, the distillate (Y) obtained in the second distillation process is subjected to a hydrogenation reaction (Reaction Scheme 1 which will follow hereinafter).

Specifically, hydrogen gas and the distillate (Y) sent from the second distillation process are supplied to a hydrogenation reactor 6, and a hydrogenation reaction is carried out in the hydrogenation reactor 6 to obtain n-propyl acetate.

According to the present exemplary embodiment, since the distillate (Y) with a low concentration of water can be subjected to a hydrogenation reaction, as described above, n-propyl acetate can be produced with a high yield.

The hydrogen gas used in the hydrogenation reaction is not particularly limited and may be a commercially available one. It is preferable to use a high-purity hydrogen gas.

Further, a supply amount of the hydrogen gas is preferably equal to or higher than the theoretical amount of hydrogen gas required for the production of n-propyl acetate from allyl acetate, more preferably in the range of 1.1 to 3.0-fold moles of the theoretical amount, and particularly preferably 1.1 to 2.0-fold moles of the theoretical amount. With the supply amount of hydrogen gas equal to or less than the theoretical amount, since when a minor reaction such as a hydrogenation decomposition reaction occurs, a given amount of hydrogen gas is consumed by the minor reaction, and hydrogen gas necessary for the major reaction is in short supply. If the supply amount of hydrogen gas is excessively high, it is disadvantageous from an economic point of view.

Examples of the catalyst (hydrogenation catalyst) used in the hydrogenation reaction include catalysts containing elements selected from Group VIII elements, Group IX elements and Group X elements of the periodic table (defined according to the 1989 IUPAC revised edition of inorganic chemical nomenclature; the same shall apply hereinafter), that is, iron, ruthenium, osmium, cobalt, rhodium, iridium, nickel, palladium or platinum.

Among these, from the viewpoint of more favorable progress of a hydrogenation reaction, it is preferable to use a catalyst containing at least one selected from platinum, palladium, rhodium, ruthenium and nickel.

The hydrogenation catalyst may be a single element (simple substance) or a single compound, or one which is supported on a carrier, if necessary. The catalyst supported on a carrier is preferable from the viewpoint of obtaining a large metal surface area, for example, upon contact of a hydrogenation catalyst with allyl acetate in a hydrogenation reaction when using a fixed-bed reactor which will be described hereinafter.

As the carrier, generally, a material used as a carrier for supporting a catalyst (for example, a porous material) may be used without particular limitation. Preferable specific examples of the carrier include silica, alumina, titanium oxide, diatomaceous earth, carbon, activated carbon, and a mixture thereof.

The carrier is preferably pellet-like or spherical for convenience in handling.

The specific surface area of the carrier is not particularly limited. The carrier preferably has a high specific surface area from the viewpoint of easily achieving favorable dispersion of a catalyst metal. More specifically, a value of the specific surface area according to a BET method is preferably in the range of 10 to 5000 $m^2/g$, more preferably 30 to 3000 $m^2/g$ and particularly preferably 50 to 2000 $m^2/g$.

Although the total pore volume of the carrier is not particularly limited, it is preferably in the range of 0.05 to 10.0 mL/g, more preferably 0.1 to 8.0 mL/g, and particularly preferably 0.5 to 5.0 mL/g.

The shape of the carrier is not particularly limited and may be appropriately selected from known shapes.

From the viewpoint of uniformity of the internal pressure of the hydrogenation reactor 6, a pellet-like, spherical, hollow cylindrical, spoke wheel-like, scale-like, honeycomb having parallel flow channel-like monolithic catalyst carrier or foamed ceramic catalyst carrier having an open-pore system is preferable. Taking into consideration convenience of the production method, a pellet shape or a spherical shape is particularly preferable.

With a carrier-supported catalyst packed in bulk on a catalyst bed, the carrier may be used such that pressure loss does not become excessive, and it is preferable to have a very high geometrical surface area as compared to a total packed volume. From these points, the carrier preferably has an outer size of 0.5 to 5.0 mm, and more preferably an outer size of 1.0 to 4.5 mm.

In the hydrogenation reaction of allyl acetate, the reaction temperature is preferably low from the viewpoint of easy suppression of a hydrogenation decomposition reaction.

The hydrogenation reaction has an extremely high calorific value (for example, a calorific value corresponding to the hydrogenation of 1 kg of allyl acetate is 1180 kJ). Therefore, when allyl acetate alone is subjected to a reaction, the temperature in the reaction system is significantly increased due to the generation of heat as a result of hydrogenation, which consequently may accelerate the hydrogenation decomposition reaction.

In order to suppress such an extreme temperature elevation, it is preferable that allyl acetate be diluted with a solvent inert to the hydrogenation reaction, followed by hydrogenation reaction.

As used herein, the term "solvent inert to the hydrogenation reaction" refers to a solvent which has substantially no effect on the hydrogenation reaction of allyl acetate in the present invention.

When allyl acetate is diluted with the inert solvent, the concentration of allyl acetate is preferably in the range of 1 to 50% by mass, more preferably 3 to 30% by mass, and most preferably 5 to 15% by mass.

If the concentration of allyl acetate is lower than 1% by mass, an extreme temperature elevation due to the generation of heat may be sufficiently suppressed, but the concentration of allyl acetate is excessively lowered, and correspondingly the productivity is decreased. On the other hand, if the concentration of allyl acetate is higher than 50% by mass, it is difficult to sufficiently suppress an extreme temperature elevation due to the generation of heat. Further, when an adiabatic liquid phase reaction (particularly, adiabatic liquid phase reaction of gas-liquid two-phase flow) is adopted, there is a high possibility that an internal temperature of the hydrogenation reactor 6 may not be controlled (for example, the temperature of the hydrogenation reactor 6 cannot be controlled to a preferable range of 0 to 200° C.).

The "solvent inert to the hydrogenation reaction" is not particularly limited and is preferably an organic solvent having no ethylenic carbon-carbon double bond (C=C bond), from the viewpoint of being not readily susceptible to hydrogenation reaction.

As shown in FIG. 1, a portion of the n-propyl acetate-containing liquid (hydrogenation reaction liquid) produced as a result of the hydrogenation reaction in the hydrogenation reactor 6 may be recycled as the inert solvent (hydrogenation reactor recycled liquid).

Specific examples of the "solvent inert to the hydrogenation reaction" include saturated esters such as ethyl acetate, n-propyl acetate, butyl acetate, isopropyl acetate, n-propyl propionate, ethyl propionate, butyl propionate and isopropyl propionate;

hydrocarbons such as cyclohexane, n-hexane and n-heptane; aromatic hydrocarbons such as benzene and toluene; ketones such as acetone and methyl ethyl ketone; halogenated hydrocarbons such as carbon tetrachloride, chloroform, methylene chloride and methyl chloride; ethers such as diethyl ether and di-n-propyl ether; alcohols such as ethanol, n-propanol, isopropanol, n-butanol and sec-butanol; amides such as N-methyl-2-pyrrolidone and N,N-dimethylacetamide.

Among these, saturated esters, hydrocarbons, or ketones are preferable from the viewpoint of less susceptibility to hydrogenation reaction and less susceptibility of allyl acetate to hydrogenation decomposition reaction. Since n-propyl acetate is produced in the present invention, recycling of this n-propyl acetate as a solvent is most preferable due to no necessity for separation of the solvent.

The hydrogenation reaction of the present invention may be any one of a gas phase reaction and a liquid phase reaction.

In the case of a gas phase reaction, the structural type of the hydrogenation reactor 6 that can be used in the present invention may be a fixed-bed reactor, a trickle-bed reactor, a moving-bed reactor, a fluidized-bed reactor, or the like. A fixed-bed reactor is most common.

In the case of a gas phase reaction, it is preferable to consider the following. Generally, heat of reaction as a result of hydrogenation is extremely large. Further, in the case of a gas phase reaction, the temperature for the introduction of reactants to the hydrogenation reactor 6 is set to a boiling point or higher. In this case, when it is intended to enhance a space-time yield, a calorific value according to hydrogenation is increased and an internal temperature of the hydrogenation reactor 6 is increased beyond a preferable reaction temperature (for example, 200° C.), which may result in acceleration of a hydrogenation decomposition reaction that is a minor reaction. A countermeasure against this may be a method of lowering a space-time yield to suppress a calorific value, or a method of controlling the temperature by means of cooling.

In the case of a liquid phase reaction, since the temperature for the introduction of reactants to the hydrogenation reactor 6 can be set to a temperature lower than the boiling point, it is advantageous for easily maintaining a preferable reaction temperature (for example, 200° C. or lower).

Specific examples of the structural type of the hydrogenation reactor 6 in the case of a liquid phase reaction include a fixed-bed type, a fluidized-bed type, and a stirred-bed type. Among these, a fixed-bed reactor is most preferable from the viewpoint of easy separation of the catalyst from the product after the reaction.

Since hydrogen gas is used in a hydrogenation reaction, a flow direction of a fluid in a liquid phase reaction using a fixed-bed reactor becomes a gas-liquid two-phase flow of a raw material-containing liquid and hydrogen gas-containing gas. The gas-liquid two-phase flow may be classified into three types of a gas-liquid countercurrent flow type, a gas-liquid cocurrent downflow type and a gas-liquid cocurrent upflow type, depending on the flow direction of raw materials of gas and liquid. In the present invention, any of them may be used. From the viewpoint of providing efficient contact between hydrogen and a catalyst which are necessary for the reaction, a gas-liquid cocurrent downflow type is most preferable.

Taken altogether, from the viewpoint of enhancing the space-time yield while suppressing hydrogenation decomposition, the most preferable reaction form of the hydrogenation reactor 6 is a liquid phase reaction of gas-liquid two-phase flow and a gas-liquid cocurrent downflow type of flow direction of the fluid.

When a reaction form of gas-liquid cocurrent downflow type using a fixed-bed reactor is employed, it is preferable to use a reactor equipped with a cooling jacket, a multitubular reactor equipped with a cooling jacket, an adiabatic reactor, or the like. Among these, an adiabatic reactor is preferable from the viewpoint of construction costs of the hydrogenation reactor 6 or a conversion rate of allyl acetate.

When the liquid phase reaction of gas-liquid two-phase flow is carried out, from the viewpoint of suppressing the hydrogenation decomposition reaction, a hydrogenation reaction as a liquid phase reaction of an adiabatic system is preferably carried out using a diluted solution of allyl acetate diluted with the above-mentioned inert solvent as a reaction liquid. This is because steps such as cooling of the hydrogenation reactor 6 are no longer essential as a result of lowering the concentration of allyl acetate in the reaction liquid.

Although the reaction temperature of a hydrogenation reaction may vary depending on the kind of raw material, it is preferably in the range of 0 to 200° C., and particularly preferably 40 to 150° C. If the reaction temperature is lower than 0° C., there is a tendency of difficulty in obtaining a sufficient reaction rate. If the reaction temperature is higher than 200° C., hydrogenation decomposition tends to readily proceed.

With regard to the reaction pressure of a hydrogenation reaction, in the case of a gas phase reaction, a sufficient activity is obtained even at normal pressure. For this reason, it is preferable to carry out the reaction at normal pressure. However, when allyl acetate is pressurized to an extent that it can be vaporized at a temperature of 200° C. or lower, the reaction may be accelerated under pressurization conditions, if necessary.

On the other hand, in the case of a liquid phase reaction of gas-liquid two-phase flow, pressurization is preferable from the viewpoint of securing a dissolved hydrogen concentration. From the viewpoint of sufficiently securing a hydrogen concentration in the hydrogenation reactor 6 through a liquid phase reaction of gas-liquid two-phase flow, a flow direction of raw materials of gas and liquid is preferably a gas-liquid cocurrent downflow type as described above.

In the case of a liquid phase reaction of gas-liquid two-phase flow, the reaction pressure is preferably in the range of 0.05 to 10 MPaG, and more preferably 0.3 to 5 MPaG.

If the reaction pressure is lower than 0.05 MPaG, there is a tendency of causing difficulty in sufficiently promoting a hydrogenation reaction. On the other hand, if the reaction pressure is higher than 10 MPaG, a hydrogenation decomposition reaction tends to readily occur.

Among these, the type of hydrogenation reaction is most preferably a reaction form a of gas-liquid cocurrent downflow type as described above, from the viewpoint of sufficiently securing a hydrogen concentration in the hydrogenation reactor 6.

According to the present exemplary embodiment described as above, the concentration of n-propyl acetate in the reaction liquid after the hydrogenation process may be preferably set to 99.00% by mass or more, more preferably 99.20% by mass or more, and particularly preferably 99.50% by mass or more.

Further, according to the present exemplary embodiment, the conversion rate of allyl acetate may be set to 99.99% or more, the selectivity of 1-propenyl acetate may be set to 0.01% or less, and the selectivity of acetic acid may be set to 1.00% or less.

Further, the concentration (by mass) of propyl propionate in the reaction liquid may be set to preferably 3000 ppm or less, more preferably 1000 ppm or less, and particularly preferably 500 ppm or less.

As described above, the method for producing n-propyl acetate in accordance with the present invention enables the production of n-propyl acetate with a high yield.

In the method for producing n-propyl acetate in accordance with the present invention, since a hydrogenation reaction of high-purity allyl acetate with a small amount of coexisting water is carried out, the production of 1-propenyl acetate as a by-product as a result of an isomerization reaction of allyl acetate, and the production of acetic acid and propane as by-products as a result of a hydrogenation decomposition reaction are suppressed.

Allyl acetate and water are simultaneously produced in an esterification reaction of allyl alcohol and acetic acid or an oxidative carboxylation reaction of propylene, acetic acid and oxygen, which is a general method for producing allyl acetate.

As described above, the inventors of the present invention found through investigations that, by an influence of water produced concurrently with allyl acetate, a minor reaction tends to easily occur in the hydrogenation reaction of allyl acetate, and the production of n-propyl acetate with a high yield becomes difficult.

Although the relationship between the concentration of water and the production amount of a by-product is not fully understood; for example, when a catalyst containing palladium (hydrogenation catalyst) is used, the interaction between allyl acetate and a palladium active site varies depending on the amount of coexisting water. As a result, it is believed that an occurrence ratio of a hydrogenation reaction (major reaction), an isomerization reaction (minor reaction) and a hydrogenation decomposition reaction (minor reaction) of allyl acetate, which are competitive reactions as shown below, is changed.

(Reaction Scheme 1) Major reaction (hydrogenation reaction of allyl acetate)

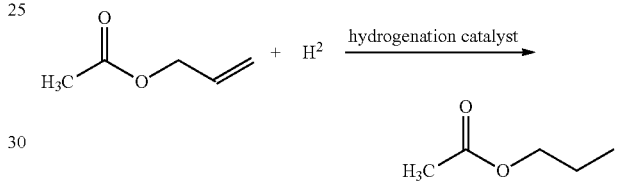

(Reaction Scheme 2) Minor reaction (isomerization reaction of allyl acetate)

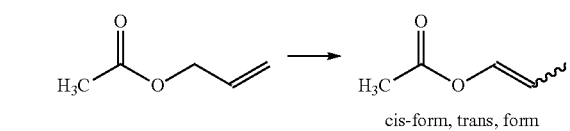

cis-form, trans, form (Reaction Scheme 3) Minor reaction (hydrogenation decomposition reaction of allyl acetate)

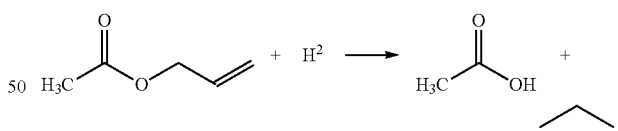

Conventionally, a distillation operation alone, or a combined method of an operation of simple oil-water separation using a decanter with a distillation operation has been used to remove water produced with the production of allyl acetate, but it is not sufficient.

On the other hand, the method for producing n-propyl acetate in accordance with the present invention is a method of carrying out an extraction operation using an extraction solvent, before a distillation operation, and actively employs the same water as the water which is an impurity, as the extraction solvent. By carrying out a distillation operation after the extraction operation, high-purity allyl acetate is obtained having a significantly low amount of coexisting water as compared to the related art.

Further, since the amount of coexisting water is small in a hydrogenation reaction of this high-purity allyl acetate, it is believed that a minor reaction (isomerization reaction, hydrogenation decomposition reaction) scarcely takes place. As a result, it is possible to produce n-propyl acetate with a high yield.

Further, since an extraction solvent is water, a waste liquid produced in the extraction process is mainly water, acetic acid and allyl acetate. This drainage treatment is convenient with a low environmental load, and such an extraction operation is a simple method.

The method for producing n-propyl acetate in accordance with the present invention is not limited to a production method shown in FIG. 1. For example, when impurities such as allyl acrylate having a boiling point close to that of allyl acetate and having a boiling point higher than that of allyl acetate are incorporated, a third distillation process of further distilling the distillate (Y) obtained in the second distillation process is preferably included between the second distillation process and the hydrogenation process. By including the third distillation process, a high-boiling point component having a boiling point higher than that of allyl acetate is removed, and consequently allyl acetate with higher purity can be obtained.

[Third Distillation Process]

In the third distillation process, the distillate (Y) obtained in the second distillation process is supplied to the third distillation column, followed by further distillation, and a distillate (Z) containing high-purity allyl acetate is obtained from the column top of the distillation column while high-boiling point components (allyl acrylate, etc.) having a boiling point higher than that of allyl acetate are removed from the column bottom.

With regard to the distillation conditions for the third distillation process, from the viewpoint of handling a material having a relatively high boiling point, the top pressure of the distillation column is preferably in the range of 0 to 200 kPaG, more preferably 0 to 50 kPaG, and the bottom pressure is preferably in the range of 20 to 220 kPaG, more preferably 20 to 70 kPaG.

The top temperature of the distillation column is preferably in the range of 100 to 130° C., more preferably 100 to 110° C., and the bottom temperature is preferably in the range of 110 to 145° C., more preferably 110 to 120° C.

The reflux ratio is preferably in the range of 0.5 to 3, more preferably 1.5 to 2, and the evaporation rate is preferably 80% by mass or more, more preferably 90% by mass or more.

By including the third distillation process, a distillate (Z) can be obtained wherein the concentrations (by mass) of allyl acrylate and acetic acid are each preferably about 10 ppm or less, more preferably about 5 ppm or less.

By using the distillate (Z) in a hydrogenation reaction, n-propyl acetate can be produced with a higher yield. Further, the production of propyl propionate as a by-product can be suppressed.

When the third distillation process is included, the concentration (by mass) of propyl propionate produced as a by-product in the reaction liquid after being subjected to a hydrogenation reaction in the hydrogenation process can be decreased to about 10 ppm or less, preferably about 5 ppm or less.

In the method for producing n-propyl acetate in accordance with the present invention, the raw material liquid containing allyl acetate and water may be a liquid which is prepared, for example, by Methods (1) to (3) as described above. Among these, Method (1) or Method (2) is preferable from the viewpoint of being capable of efficiently preparing a raw material liquid by using a simple apparatus at a low cost.

Among these, in the method for producing n-propyl acetate in accordance with the present invention, Method (1) is particularly preferable from the viewpoint of being capable of efficiently preparing a raw material liquid at a low cost. That is, a raw material liquid-preparing process of preparing the raw material liquid through an oxidative carboxylation reaction using propylene, acetic acid and oxygen gas as raw materials is preferably included before the extraction process.

[Raw Material Liquid-Preparing Process]

Figure 2:
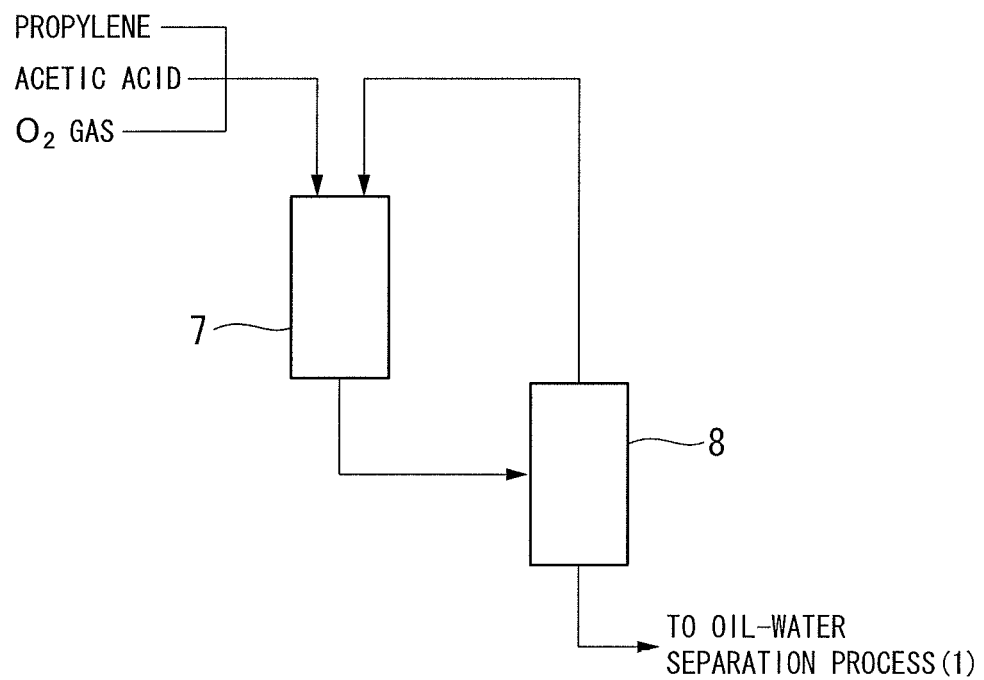
FIG. 2 is a schematic flow chart illustrating one exemplary embodiment of a process for preparing a raw material liquid.

FIG. 2 is a schematic flow chart illustrating one exemplary embodiment of a raw material liquid-preparing process, which shows a case of preparing a raw material liquid by Method (1).

The raw material liquid-preparing process in accordance with the present exemplary embodiment includes a reactor 7 for carrying out an oxidative carboxylation reaction using propylene, acetic acid and oxygen gas as raw materials, and a gas-liquid separator 8 for separating the gas components obtained from the oxidative carboxylation reaction into a condensed liquid and a non-condensed gas.

In the present exemplary embodiment, the raw material liquid obtained in the raw material liquid-preparing process is sent to an oil-water separation process (1), whereas the non-condensed gas is returned to a reactor 7 for re-utilization.

Hereinafter, Method (1) will be described.

Propylene used in Method (1) is not particularly limited. Lower saturated hydrocarbons such as propane or ethane may be included in propylene, and it is preferable to use high-purity propylene.

Oxygen gas ($O_2$) is not particularly limited and may be diluted with an inert gas such as nitrogen gas or carbon dioxide. For example, the oxygen gas may be air. However, when a reaction-produced gas is recycled, it is preferable to use a high-purity oxygen gas, particularly preferably an oxygen gas with purity of 99 vol % or more.

It is preferable to use a catalyst in the oxidative carboxylation reaction. The catalyst may be any one as long as allyl acetate is obtained by reacting propylene, acetic acid and oxygen gas. It is preferable to use a supported solid catalyst containing at least one selected from palladium, copper, lead, gold, ruthenium, an alkali metal acetate and an alkaline earth metal acetate.

Examples of the preparation method of the supported solid catalyst include an impregnation method in which an aqueous solution of a component such as a palladium salt and a component such as a copper salt is impregnated into a carrier, and then an aqueous solution of alkali metal salt is treated thereon (hereinafter, referred to as "alkali treatment"). Here, an alkali treatment is preferably carried out without drying the carrier into which the aqueous solution is impregnated. The alkali treatment time is preferably set to a time necessary for complete conversion of a component (metal salt of a catalyst component) in the aqueous solution impregnated on a carrier into a water-insoluble compound, typically about 20 hours.

Next, a metal salt of the catalyst component being made to be present on the surface layer of a carrier as a result of an alkali treatment is treated with a reducing agent, such that the metal salt becomes a zero-valent metal. A treatment with the reducing agent is carried out in a liquid phase, for example, by the addition of a reducing agent such as hydrazine or formalin. Then, the carrier is washed with water until chlorine ions or the like are not detected, followed by drying, and an alkali metal acetic acid salt is supported thereon, followed by further drying. In this manner, a supported solid catalyst can be prepared.

The carrier in the supported solid catalyst is not particularly limited, and may be any one as long as it is a porous material that is generally used as a carrier. The carrier is preferably silica, alumina, silica-alumina, diatomaceous earth, montmorillonite, titania, or the like, and more preferably silica. Further, the shape of a carrier is not particularly limited, and specific examples thereof include a powder form, a spherical shape, and a pellet shape.

The oxidative carboxylation reaction using propylene, acetic acid and oxygen gas as raw materials is carried out in a given reactor 7.

The type of a reaction when the reaction of propylene, acetic acid and oxygen gas is carried out in the presence of a catalyst may use a conventional known reaction form. Generally, since there is a reaction form which is optimal for the used catalyst, the reaction is preferably carried out in such a reaction form.

When the supported solid catalyst is used as a catalyst, it is preferable to employ a fixed-bed flow reaction where the supported solid catalyst is filled in a reactor to form a catalyst-filled layer, from the viewpoint of practical application.

A material for the reactor 7 is not particularly limited and is preferably a reactor made of an anticorrosive material.

The reaction temperature when preparing allyl acetate is preferably in the range of 100 to 300° C., and more preferably 120 to 250° C.

The reaction pressure is not particularly limited. From the viewpoint of facilities, the reaction pressure is practically advantageously in the range of 0.0 to 3.0 MPaG, and more preferably 0.1 to 1.5 MPaG.

The reaction raw material gas used as a raw material contains propylene, acetic acid and oxygen gas, and nitrogen, carbon dioxide, rare gas or the like may be used as a diluent, if necessary.

Based on the total amount of the reaction raw material gas, the amount of acetic acid is preferably in the range of 4 to 20 vol %, more preferably 6 to 10 vol %, and the amount of propylene is preferably in the range of 5 to 50 vol %, more preferably 10 to 40 vol %.

With regard to the mixing ratio of propylene, acetic acid and oxygen gas in terms of a molar ratio, the amount of propylene per mole of acetic acid is preferably in the range of 0.25 to 13 moles, more preferably 1 to 7 moles, and the amount of oxygen gas per mole of acetic acid is preferably in the range of 0.15 to 4 moles, more preferably 0.5 to 2 moles.

In a standard state, the reaction raw material gas is preferably passed through the catalyst-filled layer catalyst, at a space velocity of preferably 10 to 15000 hr$^{-1}$, and particularly preferably 300 to 8000 hr$^{-1}$.

The gas component as a result of the oxidative carboxylation reaction in the reactor 7 is cooled and then sent to a gas-liquid separator 8 where the gas component is separated into a condensed liquid and a non-condensed gas.

The condensed liquid contains acetic acid and the like, in addition to allyl acetate and water.

The non-condensed gas contains propylene, oxygen gas, and carbon dioxide as main components.

Further, the gas-liquid separator 8 may be an absorption column using acetic acid and water as an absorbing liquid. In this case, the absorbing liquid obtained by the treatment in the absorption column is combined with the condensed liquid, which serves as a raw material liquid. Then, the raw material liquid containing allyl acetate and water is sent to the oil-water separation process (1) from the bottom of the gas-liquid separator 8. On the other hand, the non-condensed gas is returned to the reactor 7 from the side opposite to the bottom of the gas-liquid separator 8, followed by re-utilization.

Hereinafter, a method for preparing a raw material liquid by an esterification reaction of allyl alcohol and carboxylic acid (2) will be described.

For example, a method for producing allyl acetate using acetic acid as a carboxylic acid can be carried out by a conventional known method.

That is, allyl acetate can be prepared by adding allyl alcohol and acetic acid to a reactor, followed by heating with stirring for several hours. Generally, the addition of an acidic material serving as a catalyst, in addition to allyl alcohol and acetic acid, is effective to increase a reaction rate.

The acidic material is not particularly limited and examples thereof include mineral acids, organic acids and solid acids or the like. Among these, hydrochloric acid, sulfuric acid, heteropolyacid, an ion-exchange resin, or the like is preferable from the viewpoint of availability and convenience of handling.

The type of a reaction is not particularly limited and may be any of a liquid phase and a gas phase and may be any of a continuous operation and a batch operation.

As a general method, there is a method in which a mixture of allyl alcohol and acetic acid is supplied to a reactor filled with a strongly acidic ion-exchange resin, followed by heating. According to this method, a mixture of allyl acetate, water, acetic acid and allyl alcohol as a raw material liquid is obtained from the reactor outlet.

The reaction pressure and reaction temperature of esterification are not particularly limited. Typically, the reaction pressure is in the range of 0 to 5.0 MPaG, and the reaction temperature is in the range of 20 to 200° C.

Further, the method for producing n-propyl acetate in accordance with the present invention may include a purification process of purifying n-propyl acetate obtained in the hydrogenation process, at the subsequent stage of the hydrogenation process.

Specifically, a portion or the total of the reaction liquid after being subjected to the hydrogenation reaction is supplied to a fourth distillation column, followed by distillation, high-boiling point components (acetic acid, propyl propionate, etc.) are removed from the column bottom, and low-boiling point components (propane gas, propionaldehyde, moisture, etc.) are removed from the column top, whereby high-purity n-propyl acetate is obtained from the middle of the fourth distillation column.

With regard to the distillation conditions for the purification process, for the purpose of separating high-boiling point components, n-propyl acetate and low-boiling point components, the top pressure of the distillation column is preferably in the range of 0 to 150 kPaG, more preferably 20 to 100 kPaG, and the bottom pressure is preferably in the range of 40 to 190 kPaG, more preferably 60 to 130 kPaG.

The top temperature of the distillation column is preferably in the range of 90 to 130° C., more preferably 100 to 130° C., and the bottom temperature is preferably in the range of 120 to 160° C., more preferably 130 to 140° C.

The reflux ratio is preferably in the range of 300 to 800, more preferably 400 to 600, and the evaporation rate is preferably 0.5% by mass or more, more preferably 1% by mass or more.

<Method for Producing n-propyl Acetate (2)>

The method for producing n-propyl acetate (2) which is a second embodiment of the present invention is a method of subjecting a raw material containing allyl acetate and water at a concentration (by mass) of 100 ppm or less to a hydrogenation reaction.

The raw material containing allyl acetate and water at a concentration (by mass) of 100 ppm or less may be prepared, for example, by the exemplary embodiment (oil-water separation process (1), extraction process, first distillation process, oil-water separation process (2), and second distillation process) shown in FIG. 1 as described above.

The hydrogenation reaction may be carried out in the same manner as in the hydrogenation reaction for the above-mentioned hydrogenation process.

<Method for Producing Allyl Acetate>

The method for producing allyl acetate in accordance with the present invention includes a reaction process of carrying out an oxidative carboxylation reaction using propylene, acetic acid and oxygen gas as raw materials, an extraction process of subjecting the reaction mixture obtained in the reaction process to an extraction operation using water as an extraction solvent and separating the extract into an oily phase and an aqueous phase, and a distillation process of distilling the oily phase.

The reaction process may be carried out, for example, in the same manner as in Method (1) as described above.

The extraction process and distillation process in the method for producing allyl acetate may be carried out in the same manner as in the extraction process and the distillation process (first distillation process, and second distillation process) as described above. Preferably, an oil-water separation process (1) is included between the reaction process and the extraction process. Further, preferably, an oil-water separation process (2) is included between the first distillation process and the second distillation process.

EXAMPLES

The present invention will be described in more detail with reference to the following Examples, but the present invention is not limited thereto.

In the following Examples, compositions of an oily phase and a distillate were analyzed according to the following method. The conversion rate of allyl acetate and the selectivity of 1-propenyl acetate and acetic acid were calculated according to the following numerical formulas.

[Analysis of Compositions of Oily Phase and Distillate]

The compositions of an oily phase and a distillate were calculated by gas chromatography (GC). The measurement conditions were as follows. Unless otherwise specified, analysis values are expressed in terms of ppm and % by mass.

(GC conditions)

Equipment: GC-17A (manufactured by Shimadzu Corporation)

Detector: Hydrogen flame ionization detector

Measurement method: Internal standard method, using 1,4-dioxane as an internal standard material.

Injection temperature: 200° C.

Temperature elevation conditions: Maintained at 40° C. for 10 minutes, elevated at a rate of 5° C./min, and then maintained at 200° C. for 30 minutes.

Column used: TC-WAX (manufactured by GL Science Inc.), inner diameter: 0.25 mm, film thickness: 0.25 μm, length: 30 m.

[Conversion Rate of Allyl Acetate]

Conversion rate of allyl acetate (%)=(moles of allyl acetate consumed in hydrogenation reaction)/(moles of allyl acetate supplied to hydrogenation reactor)×100

[Selectivity of 1-propenyl Acetate and Acetic Acid]

Selectivity of Compound A (%)=(moles of Compound A produced in hydrogenation reaction)/(moles of allyl acetate consumed in hydrogenation reaction)×100

In the formula, the term "Compound A" refers to either of 1-propenyl acetate or acetic acid.

Example 1

Raw Material Liquid-Preparing Process:

According to an impregnation method, 1 L of a catalyst was prepared wherein 5.0 g of palladium, 0.66 g of copper and 52 g of potassium acetate were supported on a 5.0-mm spherical silica carrier.

10.5 mL of the catalyst was homogeneously diluted in 31.5 mL of a silica carrier, and then filled in a reactor (made of SUS316L, inner diameter: 25 mm).

Under the conditions of a reaction temperature of 135° C. and a reaction pressure of 0.8 MPaG (gauge pressure), an oxidative carboxylation reaction was carried out by introducing a reaction raw material gas (mixed gas of propylene: oxygen gas:acetic acid:water:nitrogen gas in a volume ratio of 29:6:7.1:19:38.9) to a reactor at a space velocity of 2070 $hr^{-1}$ and passing it through a catalyst-filled layer.

Then, the gas components passed through the catalyst-filled layer were sent to a gas-liquid separator (absorption column using acetic acid and water as an absorbing liquid), and the whole quantity of the gas components was cooled. Then, among the gas components, the condensed liquid was recovered, and the non-condensed gas was treated in the absorption column. The absorbing liquid obtained by such a treatment was combined with the condensed liquid, and the combined liquid was used as a raw material liquid.

Oil-water Separation Process (1):

100 parts by mass of the raw material liquid obtained in the raw material liquid-preparing process were supplied to a decanter and then separated into two phases, 43 parts by mass of an oily phase (A1) and 57 parts by mass of aqueous phase (A1), over a residence time of 40 minutes.

Extraction Process:

Next, 43 parts by mass of the oily phase (A1) were supplied from the column bottom of an extraction column and 26 parts by mass of water as an extraction solvent were supplied from the column top of an extraction column, and the oily phase (A1) was brought into contact with water for 15 minutes in the extraction column, whereby 25 parts by mass of an oily phase (B1) containing allyl acetate as a main component and 44 parts by mass of an aqueous phase (B1) containing water as a main component were separated. The oily phase (B1) was obtained from the column top while the aqueous phase (B1) was removed from the column bottom.

First Distillation Process:

Next, 25 parts by mass of the oily phase (B1) were supplied to the first distillation column, and distilled under the following conditions: top pressure of 50 kPaG, bottom pressure of 55 kPaG, top temperature of 98° C., bottom temperature of 130° C., reflux ratio of 0.14, and evaporation rate of 90% by mass. A distillate (X1) containing allyl acetate as a main component was obtained from the column top of the distillation column while water, acetic acid and the like were removed from the column bottom.

Oil-water Separation Process (2):

Next, the distillate (X1) was supplied to a decanter, and separated into two phases, 22 parts by mass of an oily phase (C1) and 3 parts by mass of an aqueous phase (C1) over a residence time of 15 minutes. The whole quantity of the oily phase (C1) was sent to a subsequent process, and the whole quantity of the aqueous phase (C1) was returned to the first distillation column for re-utilization.

Second Distillation Process:

Next, 22 parts by mass of the oily phase (C1) were supplied to the second distillation column, and distilled under the following conditions: top pressure of 130 kPaG, bottom pressure of 140 kPaG, top temperature of 116° C., bottom temperature of 135° C., reflux ratio of 22, and evaporation rate of 5.1% by mass. 21 parts by mass of a distillate (Y1) containing allyl acetate as a main component were obtained from the column bottom of the distillation column.

The concentration of water (the concentration is by mass; the same shall apply hereinafter) in the obtained distillate (Y1) was 27 ppm, the concentration of allyl acetate was 99.62% by mass, the concentration of acetic acid was 260 ppm, and the concentration of allyl acrylate was 1100 ppm.

Hydrogenation Process:

Then, the distillate (Y1) was subjected to a hydrogenation reaction as follows.

To a cylindrical reactor having an inner diameter of 25 mm and made of SUS316L (hydrogenation reactor) was charged a hydrogenation catalyst, i.e., a 0.3% by mass palladium carbon granular catalyst 35 mL (manufactured by N.E. Chemcat Corporation) using ground activated carbon as a catalyst carrier. The interior of the hydrogenation reactor was substituted with hydrogen and then elevated up to 0.8 MPaG under a hydrogen atmosphere.

Next, a hydrogenation reaction of allyl acetate was carried out by supplying a raw material liquid made up of 5.0% by mass of the distillate (Y1) obtained in the second distillation process and 95.0% by mass of n-propyl acetate at a rate of 156 mL/hr and supplying hydrogen gas at a rate of 2.1 L/hr to the hydrogenation reactor at 40° C. by a cocurrent downflow operation, thus obtaining n-propyl acetate.

With regard to the obtained n-propyl acetate, the conversion rate of allyl acetate was 99.8%, the selectivity of n-propyl acetate was 99.49%, the selectivity of 1-propenyl acetate was 0.25%, the selectivity of acetic acid was 0.26%, and the yield of n-propyl acetate was 99.29%. In addition, the concentration of propyl propionate in the obtained reaction liquid was 56 ppm.

Example 2

Third Distillation Process:

21 parts by mass of the distillate (Y1) obtained in the second distillation process of Example 1 were supplied to a third distillation column, and distilled under the following conditions: top pressure of 5 kPaG, bottom pressure of 45 kPaG, top temperature of 105° C., bottom temperature of 135° C., reflux ratio of 1.7, and evaporation rate of 96% by mass. A distillate (Z1) containing high-purity allyl acetate was obtained from the top of the distillation column.

The concentration of water in the obtained distillate (Z1) was 30 ppm, the concentration of allyl acetate was 99.74% by mass, the concentration of acetic acid was less than 5 ppm, and the concentration of allyl acrylate was less than 5 ppm.

Hydrogenation Process:

Next, the distillate (Z1) was subjected to a hydrogenation reaction in the same manner as in Example 1, thus obtaining n-propyl acetate.

With regard to the obtained n-propyl acetate, the conversion rate of allyl acetate was 99.9%, the selectivity of 1-propenyl acetate was 0.21%, the selectivity of acetic acid was 0.25%, and the yield of n-propyl acetate was 99.97%. In addition, the concentration of propyl propionate in the obtained reaction liquid was less than 5 ppm.

Comparative Example 1

The oily phase (A1) obtained in Example 1 was supplied to a distillation column, followed by distillation, and a distillate (α) containing allyl acetate was obtained from the middle of the distillation column.

The concentration of water in the obtained distillate (α) was 2860 ppm, the concentration of allyl acetate was 99.24% by mass, the concentration of acetic acid was 270 ppm, and the concentration of allyl acrylate was 1630 ppm.

Next, the distillate (α) was subjected to a hydrogenation reaction in the same manner as in Example 1, thus obtaining n-propyl acetate.

With regard to the obtained n-propyl acetate, the conversion rate of allyl acetate was 97.1%, the selectivity of 1-propenyl acetate was 4.3%, the selectivity of acetic acid was 0.56%, and the yield of n-propyl acetate was 93.47%. In addition, the concentration of propyl propionate in the obtained reaction liquid was 83 ppm.

Comparative Example 2

The distillate (α) obtained in Comparative Example 1 was further supplied to a distillation column, followed by distillation, and a distillate (β)containing allyl acetate was obtained from the column bottom of the distillation column.

The concentration of water in the obtained distillate (β) was 282 ppm, the concentration of allyl acetate was 99.49% by mass, the concentration of acetic acid was 300 ppm, and the concentration of allyl acrylate was 1700 ppm.

Next, the distillate (β) was subjected to a hydrogenation reaction in the same manner as in Example 1, thus obtaining n-propyl acetate.

With regard to the obtained n-propyl acetate, the conversion rate of allyl acetate was 98.5%, the selectivity of 1-propenyl acetate was 2.3%, the selectivity of acetic acid was 0.33%, and the yield of n-propyl acetate was 96.56%. In addition, the concentration of propyl propionate in the obtained reaction liquid was 87 ppm.

Table 1 shows the results of composition analysis carried out for oily phase (A1), oily phase (B1), oily phase (C1), distillate (Y1), distillate (Z1), distillate (α), and distillate (β).

Table 2 shows the evaluation results for the reaction liquid obtained after the hydrogenation reaction of each example.

TABLE 1

| | | Composition (% by mass) | | | | |
| --- | --- | --- | --- | --- | --- | --- |
| | | Water | Allyl acetate | Acetic acid | Allyl acrylate | Others |
| Oil-water separation process (1) | Oily phase (A1) | 12.900 | 64.30 | 22.100 | 0.510 | 0.190 |
| Extraction process | Oily phase (B1) | 1.900 | 96.90 | 0.090 | 0.800 | 0.310 |
| Oil-water separation process (2) | Oily phase (C1) | 1.740 | 97.97 | 0.057 | 0.100 | 0.133 |
| Second distillation process | Distillate (Y1) | 27 ppm | 99.62 | 0.026 | 0.110 | 0.241 |

TABLE 1-continued

| | | Composition (% by mass) | | | | |
|---|---|---|---|---|---|---|
| | | Water | Allyl acetate | Acetic acid | Allyl acrylate | Others |
| Third distillation process | Distillate (Z1) | 30 ppm | 99.74 | Less than 5 ppm | Less than 5 ppm | 0.257 |
| Distillation operation once | Distillate (α) | 2860 ppm | 99.24 | 0.027 | 0.163 | 0.284 |
| Distillation operation twice | Distillate (β) | 282 ppm | 99.49 | 0.030 | 0.170 | 0.282 |

From the results of Table 1, it can be seen that since both of the distillate (Y1) and distillate (Z1) in accordance with the present invention exhibit a low concentration of water of less than 50 ppm and a high concentration of allyl acetate of 99.6% by mass or more, high-purity allyl acetate is obtained according to the present invention.

Further, by further including a third distillation process in the present invention, it can be seen that allyl acetate containing substantially no allyl acrylate and acetic acid is obtained.

Further, by combining an oil-water separation operation using a decanter with an extraction operation using water as an extraction solvent, it can be seen that a concentration of water contained in an oily phase can be reduced to about a level of ⅙ or less (decreased from 12.9% by mass to 1.9% by mass), as compared to an oil-water separation operation alone.

TABLE 2

| | Conversion rate of allyl acetate (%) | Yield of n-propyl acetate (%) | Selectivity of 1-propenyl acetate (%) | Selectivity of acetic acid (%) | Concentration of propyl propionate in reaction liquid (ppm, by mass) |
|---|---|---|---|---|---|
| Example 1 | 99.8 | 99.29 | 0.25 | 0.26 | 56 |
| Example 2 | 99.9 | 99.97 | 0.21 | 0.25 | Less than 5 |
| Comparative Example 1 | 97.1 | 93.47 | 4.3 | 0.56 | 83 |
| Comparative Example 2 | 98.5 | 96.56 | 2.3 | 0.33 | 87 |

From the results of Table 2, it can be seen that since the production methods of Examples 1 and 2 exhibit a high yield of n-propyl acetate of 99% by mass or more, n-propyl acetate can be produced with a high yield according to the present invention.

Further, it was demonstrated that the production methods of Examples 1 and 2 are high in terms of a conversion rate of allyl acetate and are all low in selectivity of 1-propenyl acetate, selectivity of acetic acid and concentration of propyl propionate in the reaction liquid, as compared to the production method of the Comparative Examples. From these results, it can be said that water produced simultaneously with allyl acetate has an effect on the production of impurities as a by-product in the hydrogenation reaction of allyl acetate.

[Industrial Applicability]

The present invention is applicable to a method for producing n-propyl acetate and a method for producing allyl acetate.

The invention claimed is:

1. A method for producing n-propyl acetate, comprising:
   a first oil-water separation process of separating a raw material liquid containing allyl acetate, water and acetic acid into an oily phase (A) and an aqueous phase (A);
   an extraction-separation process of subjecting the oily phase (A) to an extraction operation using water as an extraction solvent and separating the extract into an oily phase (B) containing allyl acetate as a main component and an aqueous phase (B) containing water as a main component;
   a first distillation process of distilling the oily phase (B) to obtain a distillate (X) containing allyl acetate as a main component;
   a second oil-water separation process of separating the distillate (X) into an oily phase (C) and an aqueous phase (C);
   a second distillation process of distilling the oily phase (C) to obtain a distillate (Y) containing allyl acetate as a main component; and
   a hydrogenation process of subjecting the distillate (Y) to a hydrogenation reaction,
   wherein the concentration of water (by mass) in distillate (Y) for use in the hydrogenation reaction is 100 ppm or less.

2. The method for producing n-propyl acetate according to claim 1, wherein the aqueous phase (C) is returned to the first distillation process.

3. The method for producing n-propyl acetate according to claim 1, comprising:
   a third distillation process of further distilling the distillate (Y) between the second distillation process and the hydrogenation process.

4. The method for producing n-propyl acetate according to claim 1, comprising:
   a process for preparing a raw material liquid, for preparing the raw material liquid by an oxidative carboxylation reaction using propylene, acetic acid and oxygen gas as raw materials, before the extraction process.

5. The method for producing n-propyl acetate according to claim 1, wherein a catalyst including at least one selected from platinum, palladium, rhodium, ruthenium and nickel is used in the hydrogenation reaction.

6. A method for producing allyl acetate, comprising:
   a reaction process of carrying out an oxidative carboxylation reaction using propylene, acetic acid and oxygen gas as raw materials;
   a first oil-water separation process of separating the reaction mixture obtained in the reaction process into an oily phase (A) and an aqueous phase (A);
   an extraction-separation process of subjecting the oily phase (A) to an extraction operation using water as an extraction solvent and separating the extract into an oily phase (B) containing allyl acetate as a main component and an aqueous phase (B) containing water as a main component;

a first distillation process of distilling the oily phase (B) to obtain a distillate (X) containing allyl acetate as a main component;

a second oil-water separation process of separating the distillate (X) into an oily phase (C) and an aqueous phase (C); and a second distillation process of disting the oily phase (C) to obtain a distillate (Y) containing allyl acetate as a main component, wherein the concentration of water (by mass) in the distillate (Y) is 100 ppm or less.

7. The method for producing n-propyl acetate according to claim 2, comprising:

a third distillation process of further distilling the distillate (Y) between the second distillation process and the hydrogenation process.

8. The method for producing n-propyl acetate according to claim 2, comprising:

a process for preparing a raw material liquid, for preparing the raw material liquid by an oxidative carboxylation reaction using propylene, acetic acid and oxygen gas as raw materials, before the extraction process.

9. The method for producing n-propyl acetate according to claim 2, wherein a catalyst including at least one selected from platinum, palladium, rhodium, ruthenium and nickel is used in the hydrogenation reaction.

* * * * *